(12) United States Patent
Zhang et al.

(10) Patent No.: US 10,214,532 B2
(45) Date of Patent: Feb. 26, 2019

(54) PROCESS FOR PREPARING IBRUTINIB

(71) Applicants: SHANGHAI DUDE MEDICAL SCIENCE AND TECHNOLOGY CO., LTD, Shanghai (CN); CHIA TAI TIANQING PHARMACEUTICAL GROUP CO., LTD., Lianyungang, Jiangsu Province (CN); LIANYUNGANG RUNZHONG PHARMACEUTICAL CO., LTD., Lianyungang, Jiangsu Province (CN)

(72) Inventors: Xiquan Zhang, Lianyungang (CN); Rui Kong, Shanghai (CN); Xin Liu, Shanghai (CN); Shan Chen, Shanghai (CN); Xiaoping Chen, Shanghai (CN); Leilei Yang, Lianyungang (CN); Aiming Zhang, Lianyungang (CN); Xingdong Cheng, Lianyungang (CN)

(73) Assignees: Shanghai Dude Medical Science and Technology Co., Ltd., Shanghai (CN); Chia Tai Tianqing Pharmaceutical Group Co., Ltd., Lianyungang (CN); Lianyungang Runzhong Pharmaceutical Co., Ltd., Lianyungang (CN)

( * ) Notice: Subject to any disclaimer, the term of this patent is extended or adjusted under 35 U.S.C. 154(b) by 0 days.

(21) Appl. No.: 15/549,631

(22) PCT Filed: Feb. 4, 2016

(86) PCT No.: PCT/CN2016/073537
§ 371 (c)(1),
(2) Date: Aug. 8, 2017

(87) PCT Pub. No.: WO2016/127915
PCT Pub. Date: Aug. 18, 2016

(65) Prior Publication Data
US 2018/0044339 A1 Feb. 15, 2018

(30) Foreign Application Priority Data
Feb. 12, 2015 (CN) .......................... 2015 1 0074023
Feb. 12, 2015 (CN) .......................... 2015 1 0074031
Feb. 12, 2015 (CN) .......................... 2015 1 0075177

(51) Int. Cl.
*A61K 31/519* (2006.01)
*C07D 487/04* (2006.01)

(52) U.S. Cl.
CPC ............ *C07D 487/04* (2013.01); *Y02P 20/55* (2015.11)

(58) Field of Classification Search
CPC .......................... A61K 31/519; C07D 487/04
(Continued)

(56) References Cited
U.S. PATENT DOCUMENTS
7,718,662 B1 5/2010 Chen et al.

FOREIGN PATENT DOCUMENTS
CN 101610676 A 12/2009
CN 103121999 A 5/2013
(Continued)

OTHER PUBLICATIONS
International Search Report for PCT/CN2016/073537 dated Apr. 27, 2016, 3 pages.

Primary Examiner — Jeffrey H Murray
(74) Attorney, Agent, or Firm — Kilpatrick Townsend & Stockton LLP

(57) ABSTRACT

The present application relates to a method for preparing Ibutinib as shown by the following synthetic route and the intermediate compounds involved therein.

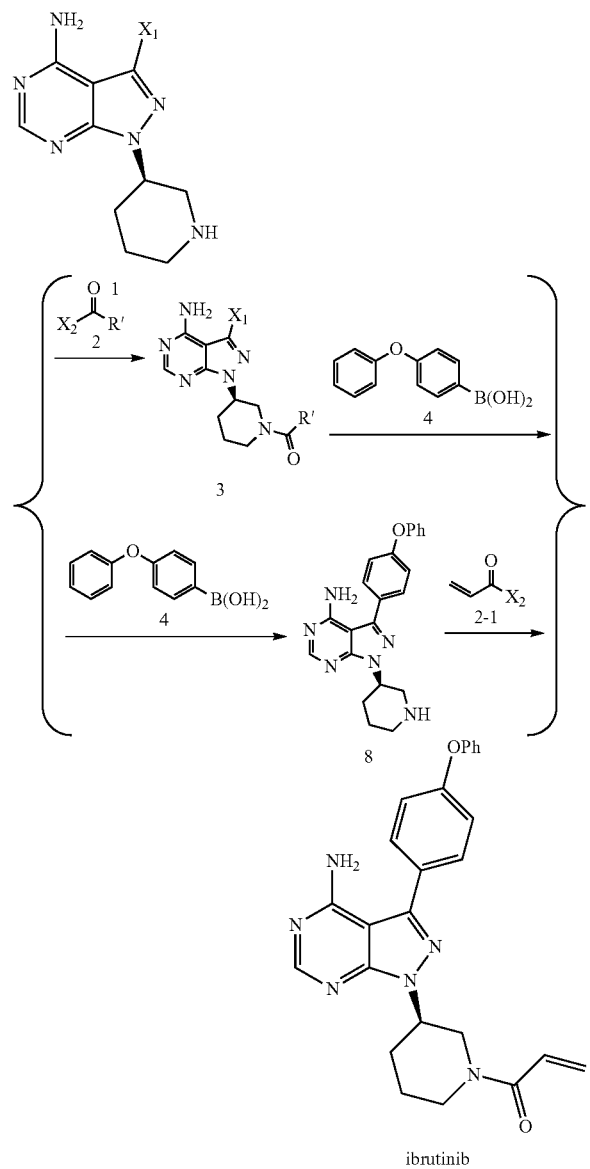

15 Claims, No Drawings

(58) Field of Classification Search
USPC .................................... 514/262.1; 544/262
See application file for complete search history.

(56) References Cited

FOREIGN PATENT DOCUMENTS

| CN | 105017256 A | 11/2015 |
|---|---|---|
| WO | 2014/188173 A1 | 11/2014 |
| WO | 2015/165279 A1 | 11/2015 |
| WO | 2016/079693 A1 | 5/2016 |

PROCESS FOR PREPARING IBRUTINIB

CROSS REFERENCE TO RELATED APPLICATIONS

This application is a 371 U.S. National Phase of PCT/CN2016/073537, international filing date Feb. 4, 2016 which claims priority to Chinese Application No. 201510074023.1, filed Feb. 12, 2015, Chinese Application No. 201510074031.6, filed Feb. 12, 2015, and Chinese Application No. 201510075177.2, filed Feb. 12, 2015, the contents of which are incorporated by reference in their entirety for all purposes.

TECHNICAL FIELD

The present application relates to the field of pharmaceutical chemistry. In particular, the present application relates to a process for preparing ibrutinib (trade name: Imbruvica) and intermediates for the preparation thereof.

BACKGROUND

Ibrutinib is an oral Bruton's tyrosine kinase (BTK) inhibitor indicated for the treatment of patients with Mantle Cell Lymphoma (MCL) who have received prior therapy, Chronic Lymphocytic Leukemia (CLL) who have received prior therapy and CLL with the 17p deletion geneticmutation (del 17p).

CN101610676A discloses that 4-phenoxybenzoic acid as a starting material was chlorinated, condensed with malononitrile and then cyclized with anhydrous hydrazine to give a pyrazole intermediate, which was then cyclized with formamide to give 4-aminopyrazolo[3,4-d]pyrimidine core, and condensed with a chiral alcohol via Mitsunobu reaction followed by the removal of the protecting group Boc and acrylation to afford a product. This synthetic route is shown as follows:

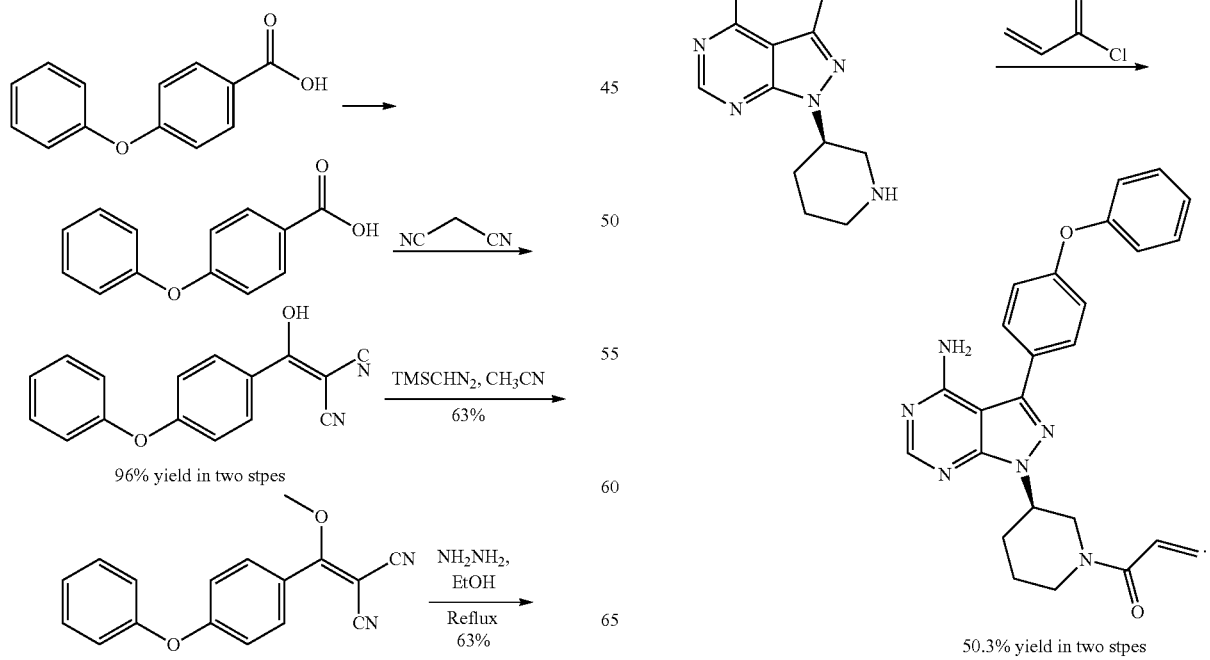

The above synthesis route is lengthy, and involves many steps. The yield in the Mitsunobu reaction step is low (34%), and the total yield is only 8.1%. Triphenylphosphine resin as an expensive and unavailable reagent is used, and purification through chromatography is finally needed to obtain ibrutinib, resulting in a high industrialization cost and complex operations.

CN103121999A discloses that 3-bromo-4-aminopyrazolo [3,4-d]pyrimidine as a starting material was coupled to 4-phenoxybenzeneboronic acid via Suzuki reaction, condensed with a chiral alcohol in the presence of cesium carbonate as a base, protected with trifluoroacetyl group, deprotected to remove the protecting group Boc, acrylated, and then deprotected to remove the protecting group trifluoroacetyl to afford ibrutinib. This synthetic route is shown as follows:

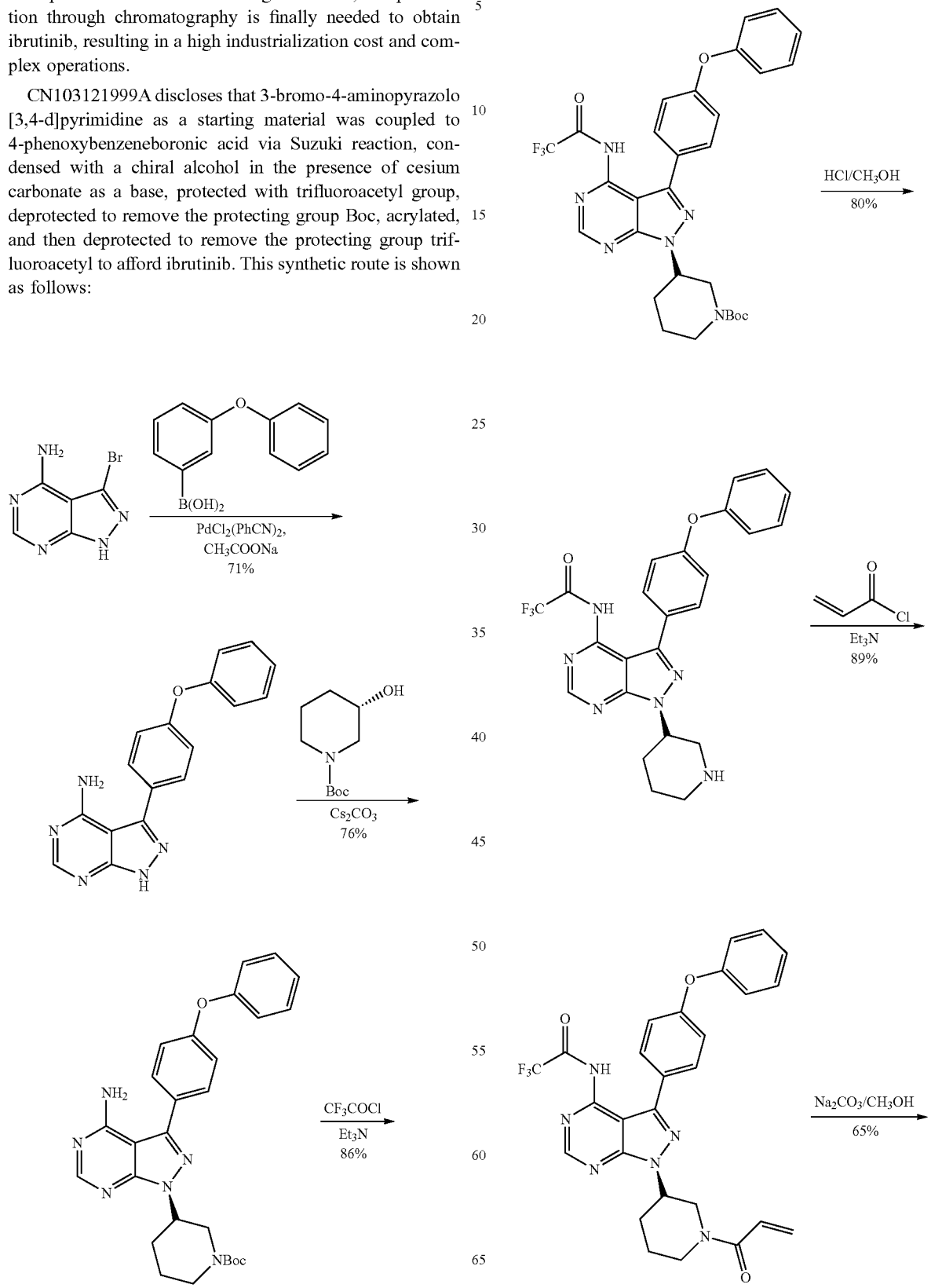

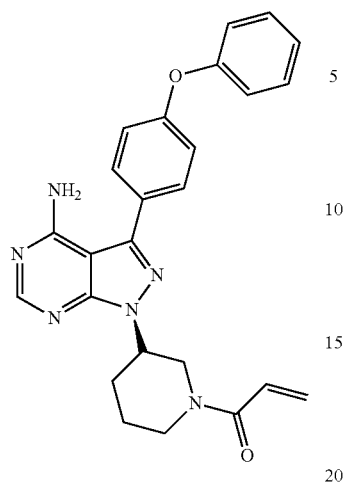

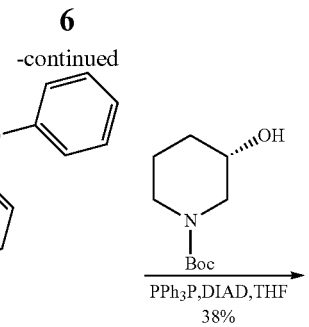

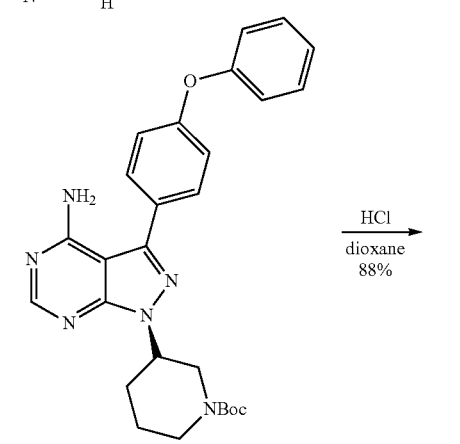

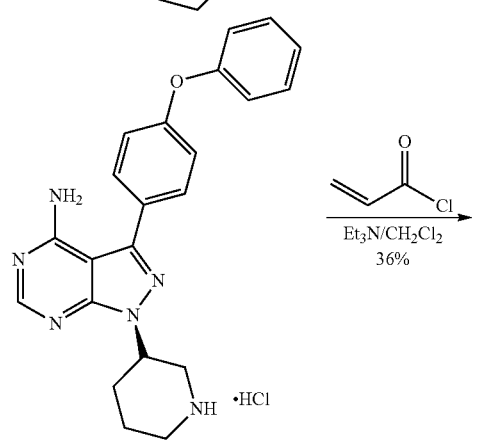

This synthesis route is also lengthy; the Suzuki reaction using PdCl₂(PhCN)₂ as a catalyst is difficult to be repeated and a large amount of the catalyst is required; it takes 24 hours to carry out the condensation step using cesium carbonate as a base, and therefore the reaction time is too long; and the steps for protection and deprotection of amino group prolong this reaction route and reduce the total yield, which was 21.5% (with 3-bromo-4-aminopyrazolo[3,4-d]pyrimidine as the starting material). Therefore, this process is not suitable for a large-scale industrial production.

WO2014022390A1 reports that 4-aminopyrazolo[3,4-d]pyrimidine as a starting material was iodinated to prepare intermediate 3-iodo-1H-pyrazolo[3,4-d]pyrimidin-4-amine, which was then coupled to 4-phenoxybenzeneboronic acid via Suzuki reaction, condensed with a chiral alcohol via Mitsunobu reaction, deprotected with hydrochloric acid to remove the protecting group Boc and form a salt, and finally acrylated to afford ibrutinib. This synthetic route is shown as follows:

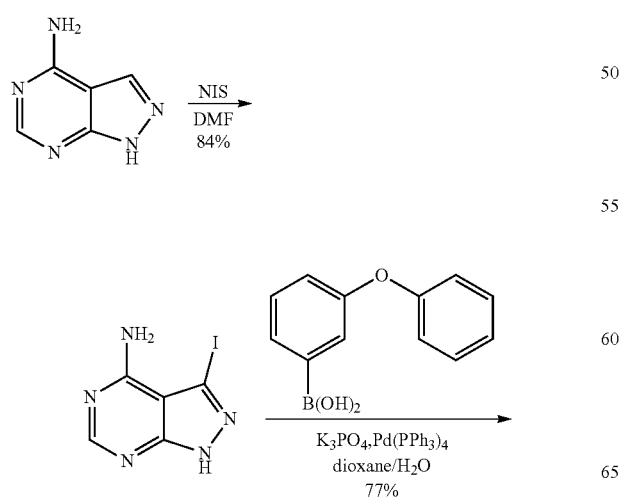

A large amount of catalyst tetraphenylphenylphosphine palladium is used in the Suzuki reaction in this synthesis route, and the reaction time is up to 24 hours; it takes a long time to carry out the Mitsunobu reaction, and its yield is low (38%); the total yield of this synthesis route is only 9.3%: and purification by chromatography is required. Therefore, this route is not suitable for industrial production, either.

In addition, commercially available acryloylchloride generally contain 1% to 3% of 3-chloropropionyl chloride, which results in the presence of 3-chloropropionylated impurities in the product ibrutinib, making the purification and industrial application difficult.

SUMMARY

In one aspect, the present application provides a process for preparing ibrutinib, comprising Step 1: reacting a compound of Formula 1 as a starting material with a compound of Formula 2 in the presence of a base to form a compound of Formula 3,

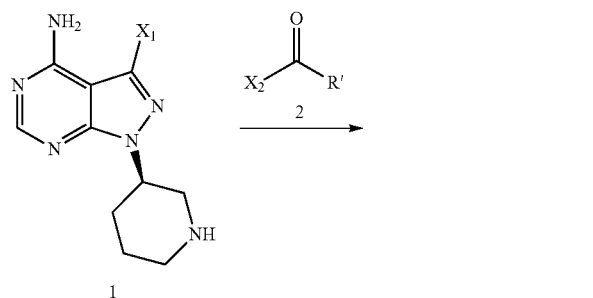

Step 2: reacting the compound of Formula 3 with a compound of Formula 4 in the presence of a base and a catalyst to produce ibrutinib,

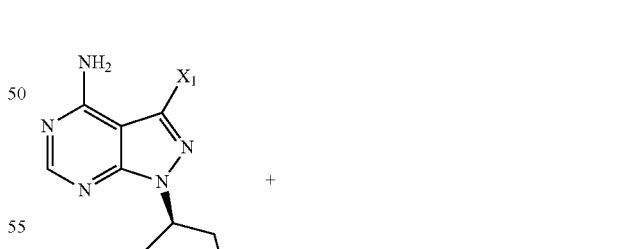

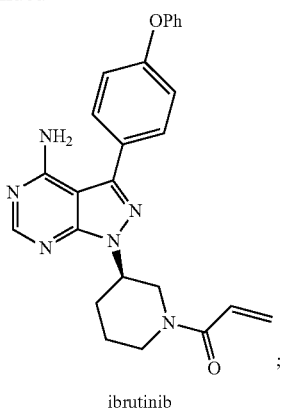

ibrutinib wherein $X_1$ is independently selected from the group consisting of Cl, Br and I, preferably Cl and Br, $X_2$ is independently selected from the group consisting of Cl and Br; R' is selected from the group consisting of

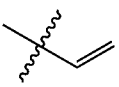 [SMILES: *C=C]

and

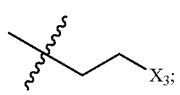

and $X_3$ is independently selected from the group consisting of Cl, Br and I, preferably Cl and Br.

In another aspect, the present application provides another process for preparing ibrutinib, comprising Step 1: reacting the compound of Formula 1 with a compound of Formula 4 in the presence of a base and a catalyst to produce a compound of Formula 8,

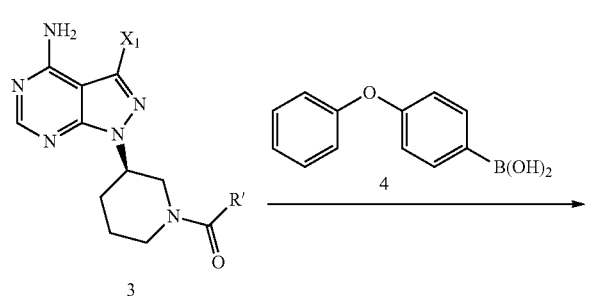

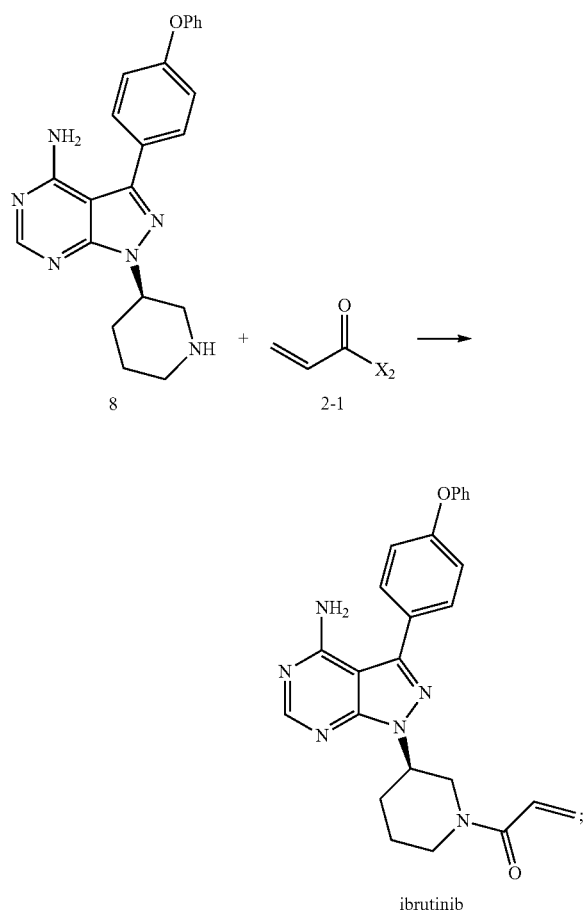

Step 2: reacting the compound of Formula 8 with a compound of Formula 2-1 in the presence of a base to produce ibrutinib, wherein $X_1$ is independently selected from the group consisting of Cl, Br and I, preferably Cl and Br, and $X_2$ is independently selected from the group consisting of Cl and Br.

In still another aspect, the present application provides an intermediate compound useful in the preparation of ibrutinib as shown below:

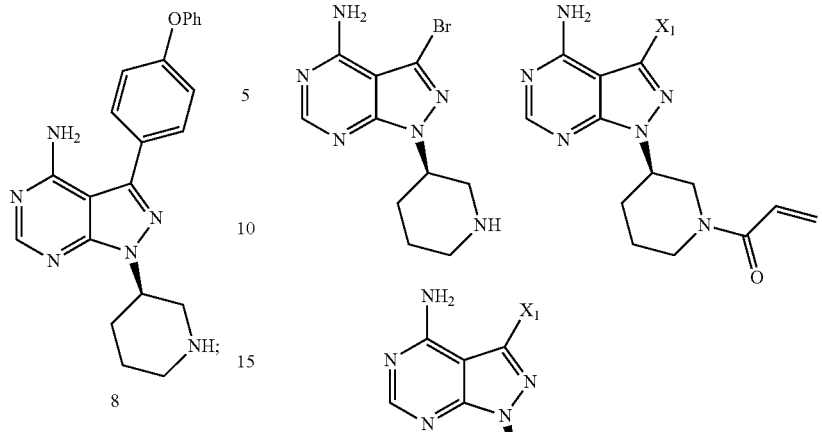

wherein $X_1$ and $X_3$ are each independently selected from the group consisting of Cl, Br and I.

In yet another aspect, the present application provides a use of an intermediate compound as shown below in the preparation of ibrutinib:

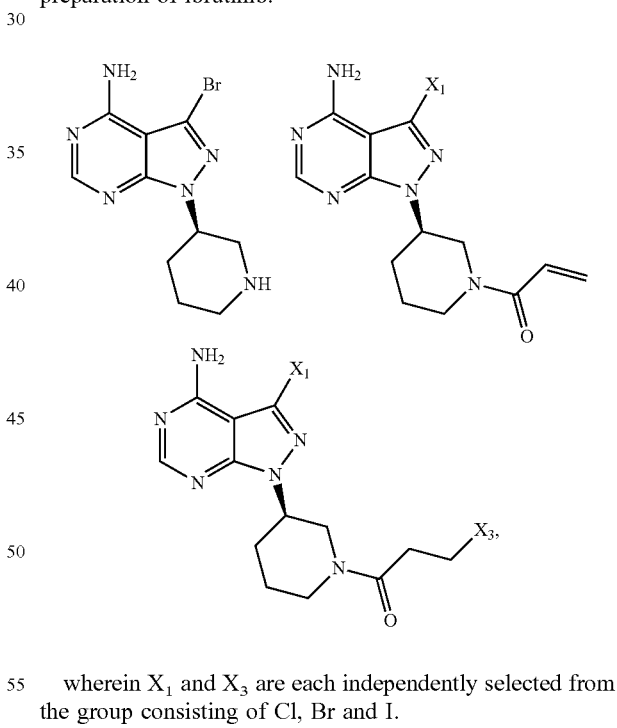

wherein $X_1$ and $X_3$ are each independently selected from the group consisting of Cl, Br and I.

DETAIL DESCRIPTION

In the following description, certain specific details are included to provide a thorough understanding of various disclosed embodiments. However, those skilled in the relevant art will recognize that the embodiments may be practiced without one or more of these specific details, or with other methods, components, materials, and the like.

Unless the context requires otherwise, throughout the specification and claims which follow, the term "comprise"

and English variations thereof, such as "comprises" and "comprising", are to be construed in an open and inclusive sense, that is as, "including, but not limited to".

Reference throughout this specification to "one embodiment", or "an embodiment", or "another embodiment", or "some embodiments" means that a particular referent element, structure, or characteristic described in connection with the embodiment is included in at least one embodiment. Accordingly, the appearances of the phase "in one embodiment", or "in an embodiment", or "in another embodiment", or "in some embodiments" in various places throughout this specification are not necessarily all referring to the same embodiment. In addition, the particular elements, structures, or characteristics may be combined in any suitable manner in one or more embodiments.

It should be noted that, as used in this specification and the appended claims, the singular forms "a", "an" and "the" include plural referents unless the content clearly dictates otherwise. Thus, for example, reference to a reaction in which "a catalyst" is involved includes a single catalyst, or two or more catalysts. Unless otherwise explicitly specified herein, it should also be noted that the term "or" is generally employed in its sense including "and/or" unless the content clearly dictates otherwise.

The present application provides a process for preparing ibrutinib, comprising

Step 1: reacting a compound of Formula 1 as a starting material with a compound of Formula 2 in the presence of a base to form a compound of Formula 3,

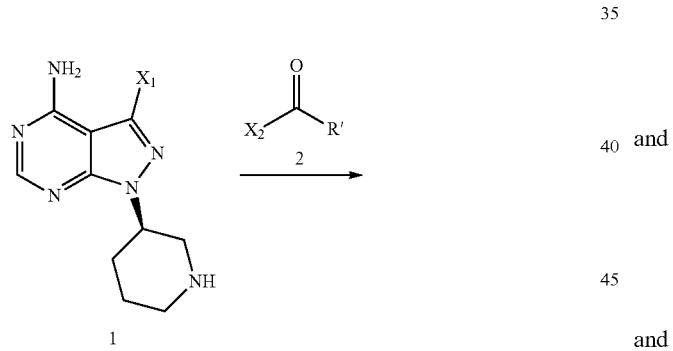

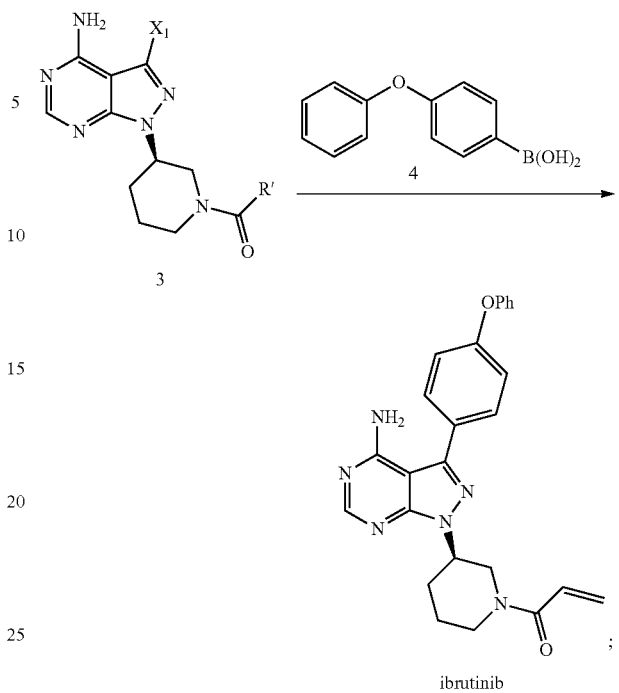

wherein $X_1$ is independently selected from the group consisting of Cl, Br and I, preferably Cl and Br, $X_2$ is independently selected from the group consisting of Cl and Br; R' is selected from the group consisting of

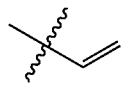

and

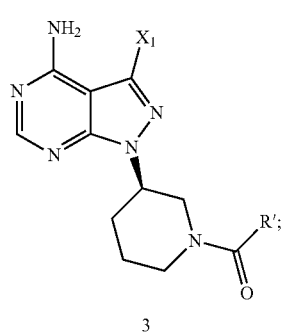

and $X_3$ is independently selected from the group consisting of Cl, Br and I, preferably Cl and Br.

In one embodiment of the present application, the amount of the compound of Formula 2 in step 1 is 0.9 to 2 equivalents, preferably 1 to 1.2 equivalents, relative to the amount of compound of Formula 1.

In one embodiment of the present application, the base used in step 1 is an inorganic base and/or an organic base, wherein the inorganic base includes, but is not limited to, potassium carbonate, sodium carbonate, sodium bicarbonate, potassium bicarbonate, sodium hydroxide, potassium hydroxide, potassium hydride or sodium hydride, and the like, and the organic base includes, but is not limited to, triethylamine, dimethylpyridine, diisopropylethylamine or 1,8-diazabicyclo[5.4.0]undec-7-ene, and the like, preferably an inorganic base, and more preferably sodium bicarbonate and potassium bicarbonate.

In one embodiment of the present application, the amount of the base used in step 1 is 1 to 5 equivalents, preferably 1.5 to 3 equivalents, and more preferably 2 equivalents, relative to the amount of the compound of Formula 1.

Step 2: reacting the compound of Formula 3 with a compound of Formula 4 in the presence of a base and a catalyst to produce ibrutinib, In one embodiment of the present application, a reaction solvent in step 1 is a polar aprotic solvent, preferably tetrahydrofuran, 2-methyltetrahydrofuran, N,N-dimethylformamide, acetonitrile or acetone, and the like, and more preferably 2-methyltetrahydrofuran.

In one embodiment of the present application, the amount of the compound of Formula 4 in step 2 is 1 to 3 equivalents, preferably 1.2 to 2 equivalents, and more preferably 1.5 equivalents, relative to the amount of compound of Formula 3.

In one embodiment of the present application, the catalyst in step 2 is selected from the group consisting of Pd(PPh$_3$)$_4$, PdCl$_2$(PPh$_3$)$_2$, PdCl$_2$(PhCN)$_2$, Pd(OAc)$_2$, Pd/C and PdCl$_2$(dppf)$_2$, and the like, preferably Pd(PPh$_3$)$_4$.

In one embodiment of the present application, the amount of the catalyst in step 2 is 0.001 to 0.1 equivalents, preferably 0.005 to 0.05 equivalents, and more preferably 0.01 equivalents, relative to the amount of the compound of Formula 3.

In one embodiment of the present application, the base used in step 2 is an inorganic base, preferably potassium carbonate, sodium carbonate, cesium carbonate, potassium acetate, sodium acetate, potassium phosphate, sodium phosphate, sodium bicarbonate, potassium bicarbonate, sodium hydroxide, potassium hydroxide, sodium hydride or potassium hydride, and more preferably potassium phosphate or potassium carbonate.

In one embodiment of the present application, the amount of the base used in step 2 is 1 to 5 equivalents, preferably 2 to 4 equivalents, and more preferably 3 to 3.5 equivalents, relative to the compound of Formula 3.

In one embodiment of the present application, an reaction solvent used in step 2 is a mixed solvent of a polar aprotic solvent and water, preferably a mixed solvent of tetrahydrofuran, 1,4-dioxane, acetonitrile, acetone, N,N-dimethylformamide (DMF), dimethylsulfoxide, N-methylpyrrolidone or ethylene glycol dimethyl ether and water, and more preferably a mixed solvent of 1,4-dioxane and water or a mixed solvent of ethylene glycol dimethyl ether and water.

In one embodiment of the present application, a reaction temperature in step 1 is 15° C. or less, preferably −10° C. to 5° C., and more preferably −5° C. to 0° C.

In one embodiment of the present application, a reaction temperature in step 2 is 60° C. to 120° C., preferably 80° C. to 100° C.

In still another aspect, the present application provides another process for preparing ibrutinib, comprising Step 1: reacting a compound of Formula 1 with a compound of Formula 4 in the presence of a base and a catalyst to produce a compound of Formula 8,

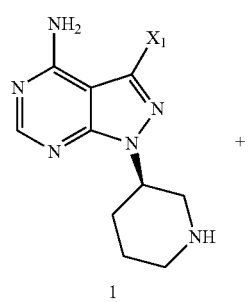

Step 2: reacting the compound of Formula 8 with a compound of Formula 2-1 in the presence of a base to produce ibrutinib, wherein X$_1$ is independently selected from the group consisting of Cl, Br and I, preferably Cl and Br; and X$_2$ is independently selected from the group consisting of Cl and Br.

In one embodiment of the present application, the amount of the compound of Formula 4 is 1 to 3 equivalents, preferably 1.2 to 2 equivalents, and more preferably 1.5 equivalents, relative to the amount of compound of Formula 1.

In one embodiment of the present application, the catalyst is selected from the group consisting of Pd(PPh$_3$)$_4$, PdCl$_2$(PPh$_3$)$_2$, PdCl$_2$(PhCN)$_2$, Pd(OAc)$_2$, Pd/C and PdCl$_2$(dppf)$_2$, and the like, preferably Pd(PPh$_3$)$_4$.

In one embodiment of the present application, the amount of the catalyst is 0.001 to 0.1 equivalents, preferably 0.005 to 0.05 equivalents, and more preferably 0.01 equivalents, relative to the amount of the compound of Formula 1.

In one embodiment of the present application, the base used in step 1 is an inorganic base, preferably potassium carbonate, sodium carbonate, cesium carbonate, potassium acetate, sodium acetate, potassium phosphate, sodium phosphate, sodium bicarbonate, potassium bicarbonate, sodium hydroxide, potassium hydroxide, sodium hydride or potassium hydride, and more preferably potassium phosphate or potassium carbonate.

In one embodiment of the present application, the amount of the base used in step 1 is 1 to 5 equivalents, preferably 2 to 4 equivalents, and more preferably 3 to 3.5 equivalents, relative to the amount of the compound of Formula 1.

In one embodiment of the present application, a reaction solvent used in step 1 is a mixed solvent of a polar aprotic solvent and water, preferably a mixed solvent of tetrahydrofuran, 1,4-dioxane, acetonitrile, acetone, N,N-dimethylformamide (DMF), dimethylsulfoxide, N-methylpyrrolidone or ethylene glycol dimethyl ether and water, and more preferably a mixed solvent of 1,4-dioxane and water or a mixed solvent of ethylene glycol dimethyl ether and water.

In one embodiment of the present application, the amount of the compound of Formula 2-1 in step 2 is 0.9 to 2 equivalents, preferably 1 to 1.2 equivalents, relative to the amount of compound of Formula 8.

In one embodiment of the present application, the base used in step 2 is an inorganic base and/or an organic base, wherein the inorganic base is selected from the group consisting of potassium carbonate, sodium carbonate, sodium bicarbonate, potassium bicarbonate, sodium hydroxide, potassium hydroxide, potassium hydride, sodium hydride and the like; and the organic base is selected from the group consisting of triethylamine, dimethylpyridine, diisopropylethylamine, 1,8-diazabicyclo[5.4.0]undec-7-ene and the like, preferably an inorganic base, and more preferably sodium bicarbonate and potassium bicarbonate.

In one embodiment of the present application, the amount of base used in step 2 is 1 to 5 equivalents, preferably 1.5 to 3 equivalents, and more preferably 2 equivalents, relative to the amount of the compound of Formula 8.

In one embodiment of the present application, a reaction solvent used in step 2 is a polar aprotic solvent, preferably tetrahydrofuran, 2-methyltetrahydrofuran, N,N-dimethylformamide, acetonitrile or acetone, and more preferably 2-methyltetrahydrofuran.

In one embodiment of the present application, a reaction temperature in step 1 is 60° C. to 120° C., preferably 80° C. to 100° C.

In one embodiment of the present application, a reaction temperature in step 2 is 15° C. or less, preferably −10° C. to 5° C., and more preferably −5° C. to 0° C.

In one embodiment of the present application, the process for preparing ibrutinib of the present application further comprises the following steps for the preparation of the compound of Formula 1:

reacting a compound of Formula 5 with a compound of Formula 6 in the presence of a Mitsunobu reaction reagent to produce a compound of Formula 7, and then deprotecting the compound of Formula 7 in the presence of an acid to produce a compound of Formula 1:

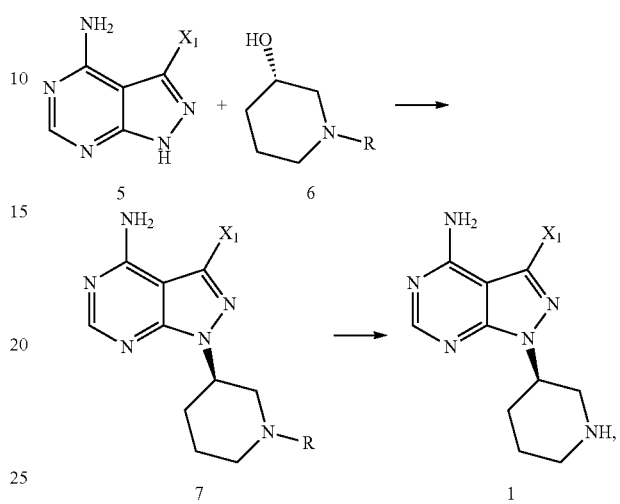

wherein R is an amino protecting group; and X$_1$ is independently selected from the group consisting of Cl, Br and I, preferably Cl or Br.

In one embodiment of the present application, the amount of the compound of Formula 6 is 0.5 to 3 equivalents, preferably 1 to 2 equivalents, and more preferably 1.5 equivalents, relative to the amount of compound of Formula 5.

In one embodiment of the present application, the Mitsunobu reaction reagent is composed of a first reagent selected from the group consisting of triphenylphosphine (TPP), tributylphosphine (TBP) and trimethylphosphine (TMP), and a second reagent selected from the group consisting of diisopropyl azodicarboxylate (DIAD), di-tert-butyl azodicarboxylate (DBAD), diethyl azodicarboxylate (DEAD), di-p-chlorobenzyl azodicarboxylate (DCAD), 1,1'-(azodicarbonyl)dipiperidine (ADDP), N,N,N',N'-tetraisopropylazodicarboxamide (TIPA), N,N,N',N'-tetramethylazodicarboxamide (TMAD) and 4,7-dimethyl-3,4,5,6,7,8-hexahydro-1,2,4,7-tetrazocin-3,8-dione (DHTD), preferably composed of TPP and DIAD.

In one embodiment of the present application, the amount of the first reagent and the amount of the second reagent in the Mitsunobu reaction reagent are equimolar to each other, and are each 1 to 5 equivalents, preferably 2 to 5 equivalents, and more preferably 3 to 4 equivalents, relative to the amount of the compound of Formula 5.

In one embodiment of the present application, a solvent used for preparing the compound of Formula 7 is selected from the group consisting of a polar aprotic solvent and water, preferably tetrahydrofuran (THF), N,N-dimethylformamide, dimethylsulfoxide, N-methylpyrrolidone, acetonitrile or 1,4-dioxane, and the like, and more preferably tetrahydrofuran.

In one embodiment of the present application, R is preferably tert-butoxycarbonyl (Boc).

In one embodiment of the present application, the acid used in deprotecting the compound of Formula 7 is selected from the group consisting of hydrochloric acid, hydrobromic acid, sulfuric acid, phosphoric acid, acetic acid, methanesulfonic acid and trifluoroacetic acid, preferably hydrochloric acid.

In another aspect, the present application provides an intermediate compound useful in the preparation of ibrutinib as shown below:

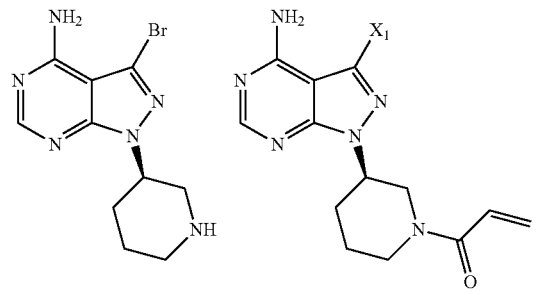

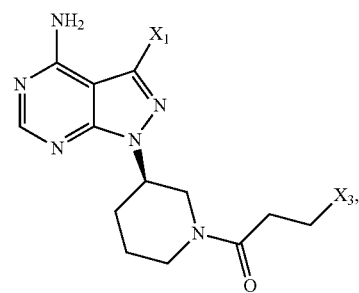

wherein $X_1$ and $X_3$ are each independently selected from the group consisting of Cl, Br and I.

In one embodiment of the present application, the intermediate compound useful in the preparation of ibrutinib is selected from the group consisting of compounds represented by the following chemical structures:

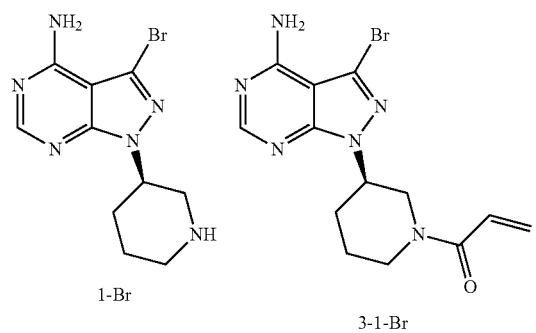

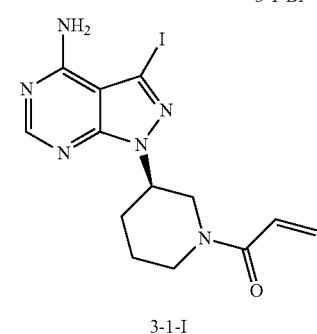

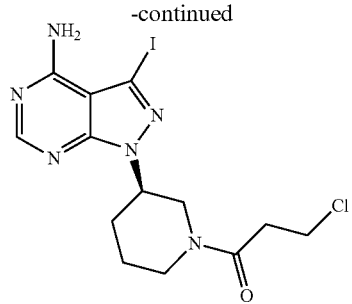

3-2-Br—Cl

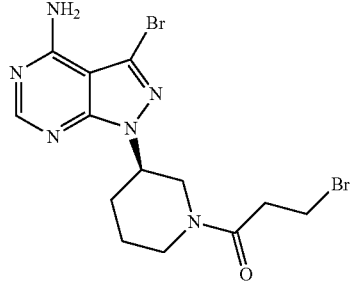

3-2-Br—Br

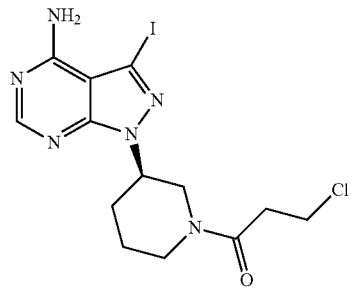 [SMILES: Nc1ncnc2c1c(I)nn2[C@@H]1CCCN(C(=O)CCCl)C1]

3-2-I—Cl

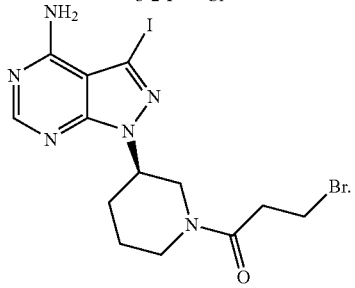

3-2-I—Br

In still another aspect, the present application provides a use of an intermediate compound as shown below in the preparation of ibrutinib:

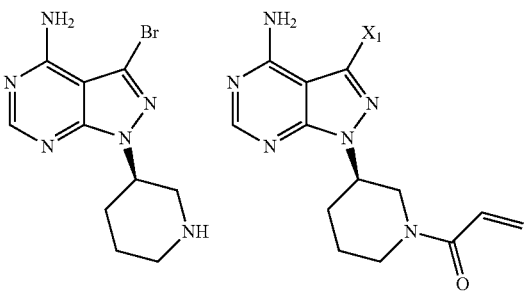

-continued

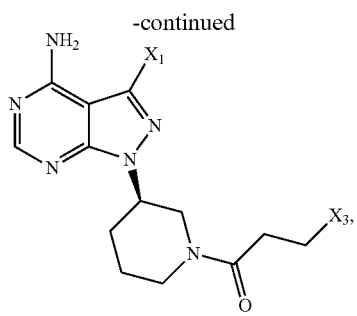

wherein $X_1$ and $X_3$ are each independently selected from the group consisting of Cl, Br and I.

In the processes for the preparation of ibrutinib of the present application, the used raw materials are inexpensive and readily available, and ibrutinib can be obtained only through acylation reaction and Suzuki reaction. The processes for preparing ibrutinib of the present application have at least one of the following advantages.

1. Acylation reaction does not require additional protection of functional groups, and the product ibrutinib can be obtained in high yield and purity.

2. The amount of the catalyst used in Suzuki reaction is much smaller than that reported in the existing literatures, and the conversion of raw materials can reach up to 100% when reacted for 1 to 5 h.

3. When Suzuki reaction occurs after the acylation reaction, the reaction for eliminating hydrogen halide can occur at the same time as Suzuki reaction, which reduces a reaction step and an impurity content of the product, and improves the total yield.

4. Where the compound of the Formula 5 is used as a starting material to carry out Mitsunobu reaction, the conversion of the starting material is significantly improved, and the reaction product can be directly precipitated from the reaction solution, which overcomes the drawback that the product of Mitsunobu reaction in the prior art needs to be purified by chromatography. Especially, when X is Br, the preparation processes of the present application can improve the yield of the final product, simplify a purification method, and reduce the cost of raw materials.

5. In the step of reacting a compound of Formula 1 with a compound of Formula 4 to produce a compound of Formula 8, the amount of a catalyst is much smaller than that reported in the prior literatures; the conversion of the raw materials can reach up to 100% when reacted for 1 to 5h; a very small amount of impurities are contained in the reaction product; and the reaction product can be purified in a high purity only by forming a corresponding salt.

In the present application, the compound of Formula 1, the compound of Formula 3 or the compound of Formula 8 may be present in the form of a free base or a salt formed with an inorganic acid or an organic acid, both of which are within the scope of the present application.

In the present application, said "equivalent" refers to the amount of a material by molar mass. For example, the amount of the compound of Formula 2 as described in the present application is 0.9 to 2 equivalents relative to the amount of the compound of Formula 1, which means that the molar mass of the compound of Formula 2 is 0.9 to 2 times relative to the molar mass of the compound of Formula 1.

EXAMPLES

The following examples are intended to illustrate the present invention, but do not constitute limitations to the scope of the present application.

Example 1

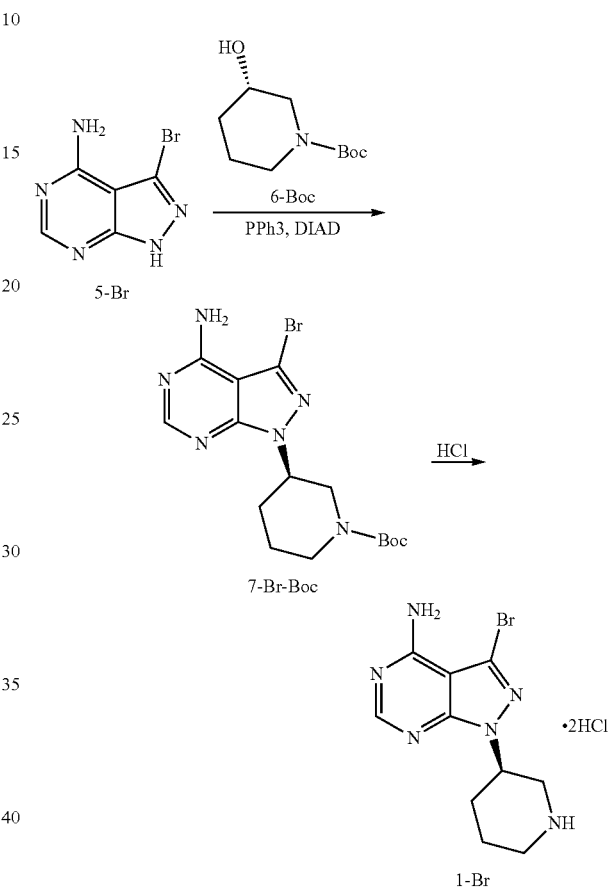

To anhydrous THF (10 eq volume) were added the compound of Formula 5-Br (60 g, 0.28 mol), the compound of Formula 6-Boc (84.6 g, 0.42 mol) and triphenylphosphine (257.4 g, 0.98 mol) under the protection of nitrogen atmosphere to obtain a pale brown suspension. A reaction temperature was reduced to 0° C., and DIAD (198.4 g, 0.98 mol) was added dropwise while keeping the temperature below 5° C. The reaction solution gradually became a pale yellow clear solution. After completing the addition, the temperature was gradually raised to 20° C., and meanwhile the reaction solution was stirred for 3 hours. Concentrated hydrochloric acid (10 eq) was added. The temperature was raised to 50° C., and the reaction solution was stirred for another 2 hours. Then, the temperature was reduced to room temperature, and the reaction mixture was filtered. The filter cake was washed with a small amount of THF, and concentrated in vacuo to dryness to constant weight to afford 74.0 g of an off-white solid in 71.0% yield and 98.5% chemical purity. To 30 g of the off-white solid was added an aqueous solution of sodium bicarbonate to afford 22.9 g of a free base in 95.1% yield and 98.5% chemical purity. m/z (MH+) 297, 1H NMR (400 MHz, DMSO) δ 1.94-2.11 (m, 4H), 2.92-2.98

(m, 1H), 3.01-3.36 (m, 2H), 3.45-3.47 (m, 1H), 5.12-5.19 (m, 1H), 8.50-8.51 (s, 1H), 9.61-9.87 (dd, 2H).

Example 2

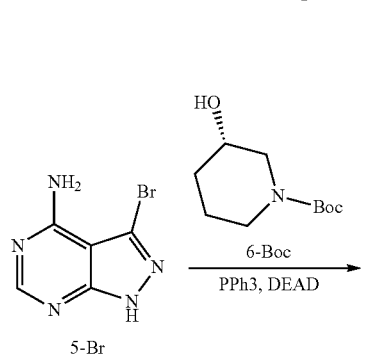

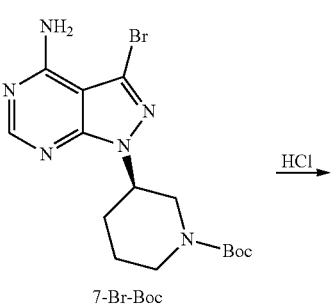

To anhydrous THF (10 eq volume) were added the compound of Formula 5-Br (60 g, 0.28 mol), the compound of Formula 6-Boc (84.6 g, 0.42 mol) and triphenylphosphine (257.4 g, 0.98 mol) under the protection of nitrogen atmosphere to obtain a pale brown suspension. A reaction temperature was reduced to 0° C., and DEAD (170.8 g, 0.98 mol) was added dropwise while keeping the temperature below 5° C. The reaction solution gradually became a pale yellow clear solution. After completing the addition, the temperature was gradually raised to 20° C., and meanwhile the reaction solution was stirred for 3 hours. Concentrated hydrochloric acid (10 eq) was added. The temperature was raised to 50° C., and the reaction solution was stirred for another 2 hours. Then, the temperature was reduced to room temperature, and the reaction mixture was filtered. The filter cake was washed with a small amount of THF, and concentrated in vacuo to dryness to constant weight to afford 70.3 g of an off-white solid in 67.8% yield and 98.3% chemical purity.

Example 3

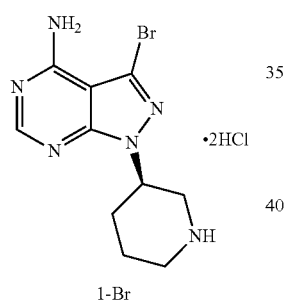

To anhydrous THF (200 mL) were added the compound of Formula 5-Br (20 g, 0.093 mol), the compound of Formula 6-Boc (28.21 g, 0.14 mol) and triphenylphosphine (85.79 g, 0.33 mol) under the protection of nitrogen atmosphere to obtain a pale brown suspension. A reaction temperature was reduced to 0° C., and DIAD (66.14 g, 0.33 mol) was added dropwise while keeping the temperature below 5° C. The reaction solution gradually became a pale yellow clear solution. After completing the addition, the temperature was gradually raised to 0° C. to 10° C., and meanwhile the reaction solution was stirred for 3 hours. Concentrated hydrochloric acid (78 mL) was added. The temperature was raised to 50° C., and the reaction solution was stirred for another 2 hours. Then, the temperature was reduced to room temperature, and the reaction mixture was filtered. After water was added to dissolve the filter cake, the solution was adjusted to pH 8 with 6N sodium hydroxide solution, and extracted with dichloromethane. The organic phase was dried over anhydrous sodium sulfate, filtered and concentrated in vacuo to dryness to afford 19.5 g of an off-white solid in 70% yield.

Example 4

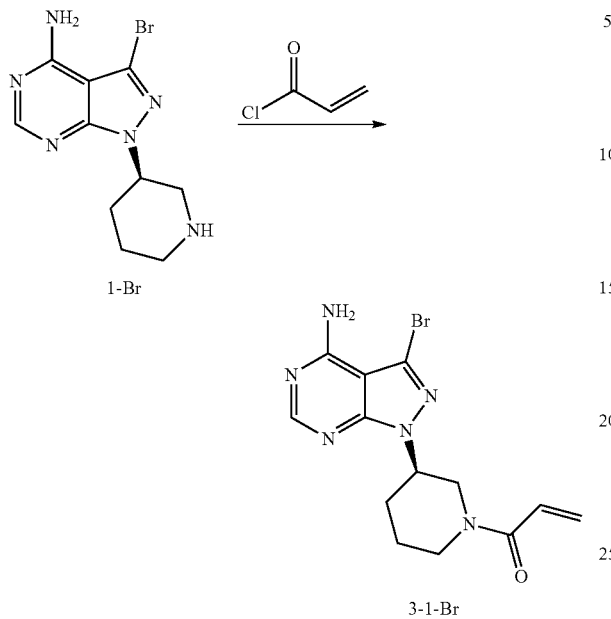

The compound of Formula 1-Br (5 g, 0.017 mol) was dissolved in 2-methyltetrahydrofuran (50 mL), and a 7% aqueous solution (40 mL) of sodium bicarbonate (2.83 g, 0.034 mol) was added under the protection of nitrogen atmosphere. The reaction temperature was then reduced to −5° C., and a solution of acryloyl chloride (1.52 g, 0.017 mol) in 2-methyltetrahydrofuran (5 mL) was slowly added dropwise. After completing the addition, the reaction temperature was kept below 0° C., and meanwhile the reaction solution was stirred for 1 h. The reaction solution was layered. After the aqueous phase was extracted with 2-methyltetrahydrofuran (50 mL), the organic phases were combined, washed sequentially with a 7% aqueous solution (50 mL) of sodium bicarbonate and water (50 mL), dried over anhydrous sodium sulfate, and concentrated in vacuo to dryness to afford 5.03 g of a pale yellow solid in 85.1% yield, which contained 1.05% of impurity

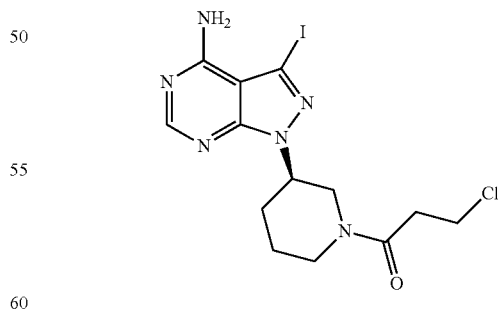

detected by HPLC. m/z (MH+) 351, 1H NMR (400 MHz, DMSO) δ 1.56-1.59 (m, 1H), 1.88-1.99 (m, 1H), 2.05-2.22 (m, 3H), 2.91 (m, 0.5H) & 3.59-3.62 (m, 0.5H), 3.07-3.19 (m, 1H), 4.05-4.08 (m, 0.5H) & 4.51-4.57 (m, 0.5H), 4.60-4.63 (m, 1H), 5.61-6.15 (dd, 2H), 6.69-6.88 (m, 1H), 8.23 (s, 1H).

Example 5

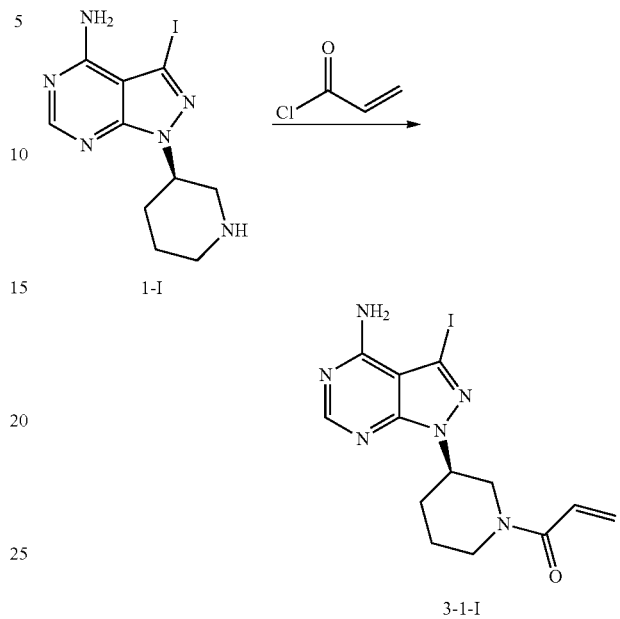

The compound of Formula 1-I (5 g, 0.0145 mol) was dissolved in 2-methyltetrahydrofuran (50 mL), and a 7% aqueous solution (34.8 mL) of sodium bicarbonate (2.44 g, 0.029 mol) was added under the protection of nitrogen atmosphere. The reaction temperature was then reduced to −5° C., and a solution of acryloyl chloride (1.31 g, 0.0145 mol) in 2-methyltetrahydrofuran (5 mL) was slowly added dropwise. After completing the addition, the reaction temperature was kept below 0° C., and meanwhile the reaction solution was stirred for 1 h. The reaction solution was layered. After the aqueous phase was extracted with 2-methyltetrahydrofuran (50 mL), the organic phases were combined, washed sequentially with a 7% aqueous solution (50 mL) of sodium bicarbonate and water (50 mL), dried over anhydrous sodium sulfate, and concentrated in vacuo to dryness to afford 4.67 g of a pale yellow solid in 80.7% yield, which contained 1.01% of impurity detected by HPLC. m/z (MH+), 1H NMR (400 MHz, DMSO) δ 8.22 (s, 1H), 6.82-6.86 (m, 1H), 6.11-6.15 (m, 1H), 5.63-5.72 (m, 1H), 4.63-4.69 (m, 1H), 4.05-4.19 (m, 0.5H), 4.59-4.63 (m, 0.5H), 3.84 (m, 0.5H), 3.10-3.16 (m, 1H), 1.85-1.94 (m, 2H), 2.04-2.08 (m, 1H), 1.55-1.58 (m, 1H).

Example 6

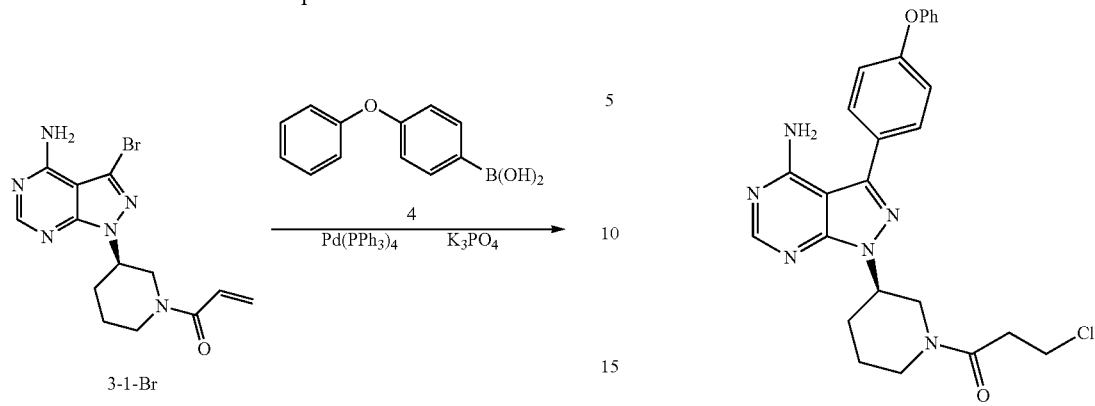

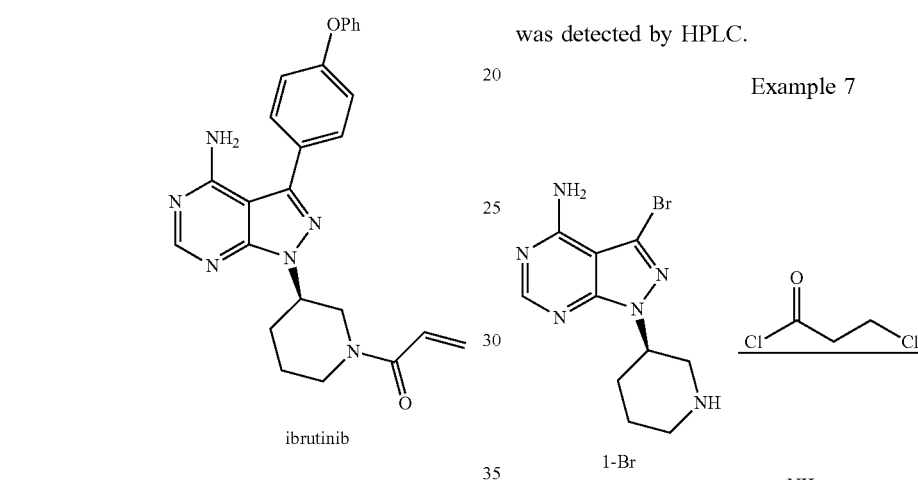

To a mixed solvent of 1,4-dioxane (30 mL) and water (12 mL) were added the compound of Formula 3-1-Br (3 g, 8.54 mmol) (it contained 1.05% of impurity detected by HPLC) obtained in Example 4, the compound of Formula 4 (2.74 g, 12.81 mmol) and potassium phosphate (5.44 g, 25.63 mmol). After bubbling with nitrogen gas for 20 min, Pd(PPh$_3$)$_4$ (98.7 mg, 0.085 mmol) was added, and bubbling with nitrogen was continued for 5 min. The reaction mixture was heated to reflux for 1 h under stirring, and thereafter was layered. After the organic phase was evaporated to dryness, the residue was crystallized in ethanol to afford 3.2 g of an off-white solid in 85% yield and 99.8% purity, and no impurity was detected by HPLC.

Example 7

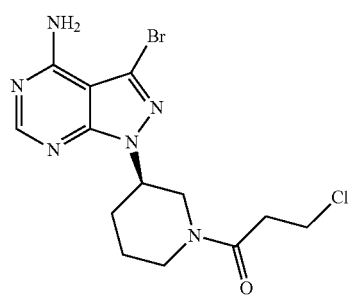 [SMILES: Nc1ncnc2c1c(Br)nn2[C@@H]1CCCN(C(=O)CCCl)C1]

The compound of Formula 1-Br (5 g, 0.017 mol) was dissolved in 2-methyltetrahydrofuran (50 mL), and a 7% aqueous solution (40 mL) of sodium bicarbonate (2.83 g, 0.034 mol) was added under the protection of nitrogen atmosphere. The reaction temperature was then reduced to −5° C., and a solution of 3-chloropropionyl chloride (2.14 g, 0.017 mol) in 2-methyltetrahydrofuran (5 mL) was slowly added dropwise. After completing the addition, the reaction temperature was kept below 0° C., and meanwhile the reaction solution was stirred for 1 h. The reaction solution was layered. After the aqueous phase was extracted with 2-methyltetrahydrofuran (50 mL), the organic phases were combined, washed sequentially with a 7% aqueous solution (50 mL) of sodium bicarbonate and water (50 mL), dried over anhydrous sodium sulfate, and concentrated in vacuo to dryness to afford 5.61 g of a pale yellow solid in 86.6% yield. m/z (MH+) 1H NMR (400 MHz, DMSO) δ 8.24 (s, 1H), 4.47-4.56 (m, 1H), 4.00-4.04 (m, 1H), 4.69 (m, 0.5H), 4.21-4.27 (m, 0.5H), 3.80-3.82 (m, 0.5H), 3.51-3.57 (m, 0.5H), 3.76-3.80 (m, 1H), 2.70-3.14 (m, 4H), 2.05-2.16 (m, 2H), 1.48-1.64 (m, 2H).

Example 8

The compound of Formula 1-Br (5 g, 0.017 mol) was dissolved in 2-methyltetrahydrofuran (50 mL), and a 7% aqueous solution (40 mL) of sodium bicarbonate (2.83 g, 0.034 mol) was added under the protection of nitrogen atmosphere. The reaction temperature was then reduced to −5° C., and a solution of 3-bromopropionyl bromide (3.63 g, 0.017 mol) in 2-methyltetrahydrofuran (5 mL) was slowly added dropwise. After completing the addition, the reaction temperature was kept below 0° C., and meanwhile the reaction solution was stirred for 1 h. The reaction solution was layered. After the aqueous phase was extracted with 2-methyltetrahydrofuran (50 mL), the organic phases were combined, washed sequentially with a 7% aqueous solution (50 mL) of sodium bicarbonate and water (50 mL), dried over anhydrous sodium sulfate, and concentrated in vacuo to dryness to afford 6.12 g of a pale yellow solid in 84.1% yield. m/z (MH+) 1H NMR (400 MHz, DMSO) δ 8.31 (s, 1H), 4.71-4.76 (m, 1H), 4.48-4.59 (m, 1H), 4.20-4.23 (m, 0.5H), 4.00-4.02 (m, 0.5H), 3.86-3.89 (m, 0.5H), 3.51-3.55 (m, 0.5H), 3.55-3.67 (m, 1H), 2.81-3.17 (m, 1H), 2.06-2.21 (m, 2H), 1.81-1.91 (m, 1H), 1.46-1.68 (m, 1H).

Example 9

The compound of Formula 1-I (5 g, 0.0145 mol) was dissolved in 2-methyltetrahydrofuran (50 mL), and a 7% aqueous solution (34.8 mL) of sodium bicarbonate (2.44 g, 0.029 mol) was added under the protection of nitrogen atmosphere. The reaction temperature was then reduced to −5° C., and a solution of 3-chloropropionyl chloride (1.84 g, 0.0145 mol) in 2-methyltetrahydrofuran (5 mL) was slowly added dropwise. After completing the addition, the reaction temperature was kept below 0° C., and meanwhile the reaction solution was stirred for 1 h. The reaction solution was layered. After the aqueous phase was extracted with 2-methyltetrahydrofuran (50 mL), the organic phases were combined, washed sequentially with a 7% aqueous solution (50 mL) of sodium bicarbonate and water (50 mL), dried over anhydrous sodium sulfate, and concentrated in vacuo to dryness to afford 5.29 g of a pale yellow solid in 83.8% yield. m/z (MH+), 1H NMR (400 MHz, DMSO) δ 8.23 (s, 1H), 4.66-4.71 (m, 0.5H), 4.47-4.58 (m, 1H), 4.21-4.24 (m, 0.5H), 3.99-4.03 (m, 0.5H), 3.87-3.90 (m, 0.5H), 3.76-3.82 (m, 2H), 2.71-3.15 (m, 4H), 1.99-2.21 (m, 2H), 1.80-1.89 (m, 1H), 1.48-1.64 (m, 1H).

Example 10

The compound of Formula 1-I (5 g, 0.0145 mol) was dissolved in 2-methyltetrahydrofuran (50 mL), and a 7% aqueous solution (34.8 mL) of sodium bicarbonate (2.44 g, 0.029 mol) was added under the protection of nitrogen atmosphere. The reaction temperature was then reduced to −5° C., and a solution of 3-bromopropionyl bromide (3.14 g, 0.0145 mol) in 2-methyltetrahydrofuran (5 mL) was slowly added dropwise. After completing the addition, the reaction temperature was kept below 0° C., and meanwhile the reaction solution was stirred for 1 h. The reaction solution was layered. After the aqueous phase was extracted with 2-methyltetrahydrofuran (50 mL), the organic phases were combined, washed sequentially with a 7% aqueous solution (50 mL) of sodium bicarbonate and water (50 mL), dried over anhydrous sodium sulfate, and concentrated in vacuo to dryness to afford 6.01 g of a pale yellow solid in 86.3% yield. m/z (MH+), 1H NMR (400 MHz, DMSO) δ 8.23 (s, 1H), 4.69 (m, 0.5H), 4.47-4.55 (m, 1H), 4.20-4.24 (m, 0.5H), 3.97-3.98 (m, 0.5H), 3.86-3.89 (m, 0.5H), 3.52-3.67 (m, 2H), 2.83-3.12 (m, 4H), 2.06-2.19 (m, 2H), 1.86-1.89 (m, 1H), 1.64-1.84 (m, 1H).

Example 11

Example 12

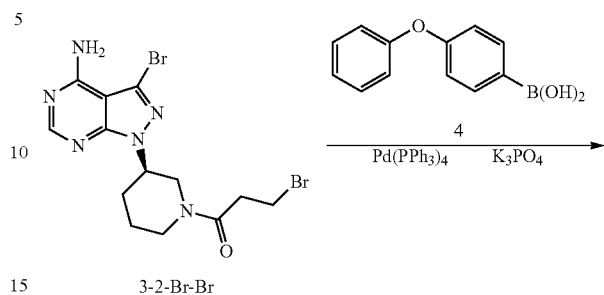

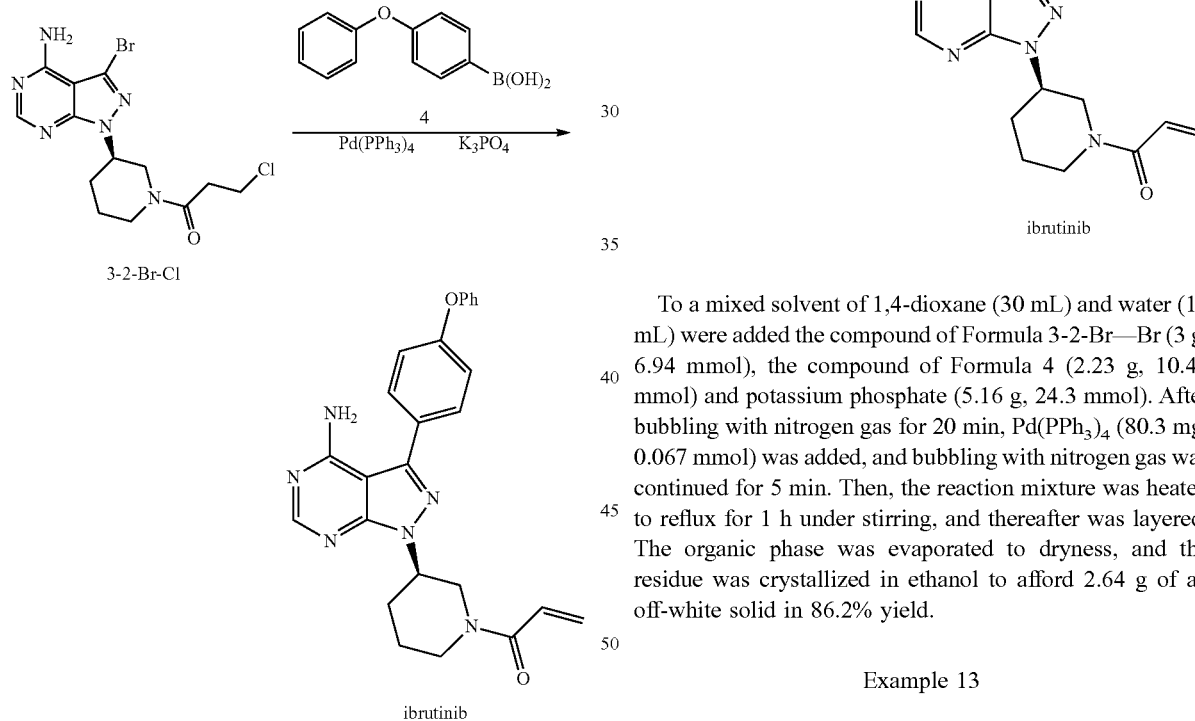

To a mixed solvent of 1,4-dioxane (30 mL) and water (12 mL) were added the compound of Formula 3-2-Br—Br (3 g, 6.94 mmol), the compound of Formula 4 (2.23 g, 10.41 mmol) and potassium phosphate (5.16 g, 24.3 mmol). After bubbling with nitrogen gas for 20 min, Pd(PPh$_3$)$_4$ (80.3 mg, 0.067 mmol) was added, and bubbling with nitrogen gas was continued for 5 min. Then, the reaction mixture was heated to reflux for 1 h under stirring, and thereafter was layered. The organic phase was evaporated to dryness, and the residue was crystallized in ethanol to afford 2.64 g of an off-white solid in 86.2% yield.

Example 13

To a mixed solvent of 1,4-dioxane (30 mL) and water (12 mL) were added the compound of Formula 3-2-Br—Cl (3 g, 7.74 mmol), the compound of Formula 4 (2.48 g, 11.61 mmol) and potassium phosphate (5.75 g, 27.09 mmol). After bubbling with nitrogen gas for 20 min, Pd(PPh$_3$)$_4$ (89.4 mg, 0.077 mmol) was added, and bubbling with nitrogen gas was continued for 5 min. Then, the reaction mixture was heated to reflux for 1 h under stirring, and thereafter was layered. The organic phase was evaporated to dryness, and the residue was crystallized in ethanol to afford 2.87 g of an off-white solid in 84.2% yield.

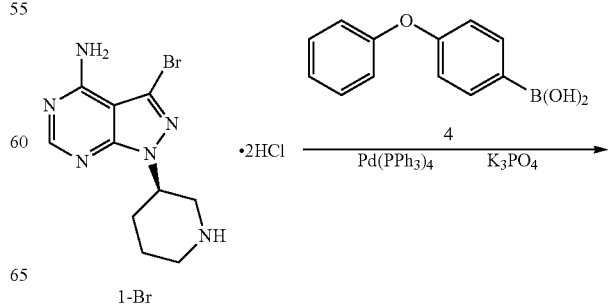

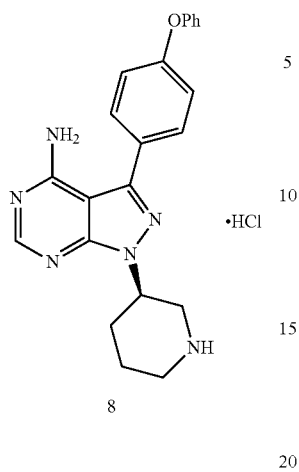

8

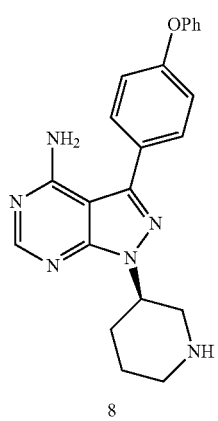

8

To a mixed solvent of 1,4-dioxane (200 mL) and water (80 mL) were added the dihydrochloride of the compound of Formula 1-Br (20 g, 0.054 mol), the compound of Formula 4 (17.35 g, 0.081 mol) and potassium phosphate (40.15 g, 0.19 mol). After bubbling with nitrogen gas for 20 min, Pd(PPh$_3$)$_4$ (0.62 g, 5.4×10$^{-4}$ mol) was added, and bubbling with nitrogen gas was continued for 5 min. The reaction solution was heated to reflux for 5 h under stirring, and then concentrated. Ethyl acetate (100 mL) and water (100 mL) were added to the residue. The resulting solution was layered after the pH was adjusted to 2 to 3 with hydrochloric acid, and then the aqueous phase was extracted once with ethyl acetate (100 mL). After liquid separation, dichloromethane (200 mL) was added to the aqueous phase, and the pH was adjusted to 9 to 10 with 6N sodium hydroxide solution. The resulting solution was stirred for liquid separation. The organic layer was dried over anhydrous sodium sulfate, and the solvent was evaporated to dryness to afford 18.8 g of a free base of Compound 8 as an off-white solid in 90.0% yield and 98.5% chemical purity. The free base was reacted with a solution of HCl in ethanol to form a salt, and 18.9 g of the hydrochloride of Compound 8 was obtained in 92% yield and 99.1% chemical purity.

Example 14

To a mixed solvent of ethylene glycol dimethyl ether (200 mL) and water (80 mL) were added the compound of the formula 1-Br (16.1 g, 0.054 mol), the compound of Formula 4 (17.35 g, 0.081 mol) and potassium phosphate (48.5 g, 0.23 mol). After bubbling with nitrogen gas for 20 min, Pd(PPh$_3$)$_4$ (0.62 g, 5.4×10$^{-4}$ mol) was added, and bubbling with nitrogen gas was continued for 5 min. The reaction solution was heated to reflux for 5 h under stirring, and then concentrated. Ethyl acetate (100 mL) and water (100 mL) were added to the residue. The resulting solution was layered after the pH was adjusted to 2 to 3 with hydrochloric acid, and then the aqueous phase was extracted once with ethyl acetate (100 mL). After liquid separation, dichloromethane (200 mL) was added to the aqueous phase, and the pH was adjusted to 9 to 10 with 6N sodium hydroxide solution. The resulting solution was stirred for liquid separation. The organic layer was dried over anhydrous sodium sulfate, and the solvent was evaporated to dryness to afford 18.2 g of a free base of Compound 8 as an off-white solid in 87.1% yield and 98.8% chemical purity.

Example 15

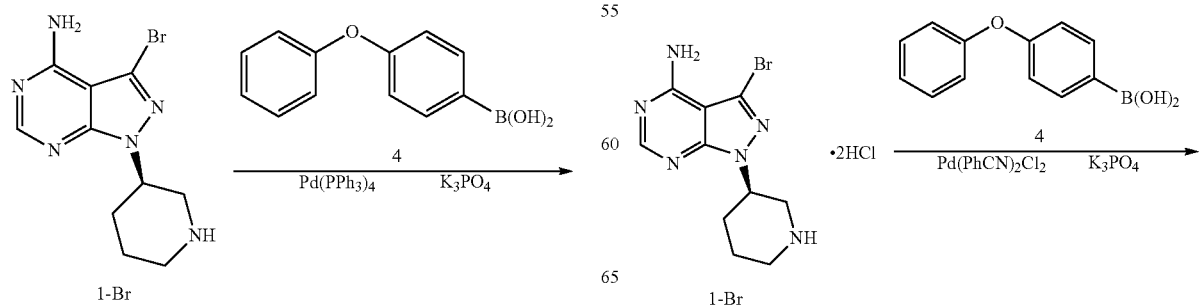

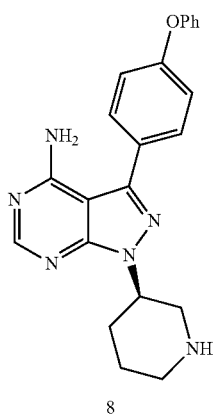

8

To a mixed solvent of DMF (200 mL) and water (80 mL) were added the dihydrochloride of the compound of Formula 1-Br (20 g, 0.054 mol), the compound of Formula 4 (17.35 g, 0.081 mol) and potassium phosphate (40.15 g, 0.19 mol). After bubbling with nitrogen gas for 20 min, Pd(PhCN)$_2$Cl$_2$ (0.21 g, 5.5×10$^{-4}$ mol) was added, and bubbling with nitrogen gas was continued for 5 min. The solution reaction was heated to reflux for 5 h under stirring, and then concentrated. Ethyl acetate (100 mL) and water (100 mL) were added to the residue. The resulting solution was layered after the pH was adjusted to 2 to 3 with hydrochloric acid, and then the aqueous phase was extracted once with ethyl acetate (100 mL). After liquid separation, dichloromethane (200 mL) was added to the aqueous phase, and the pH was adjusted to 9 to 10 with 6N sodium hydroxide solution. The resulting solution was stirred for liquid separation. The organic layer was dried over anhydrous sodium sulfate, and the solvent was evaporated to dryness to afford 13.6 g of an off-white solid in 65.1% yield.

Example 16

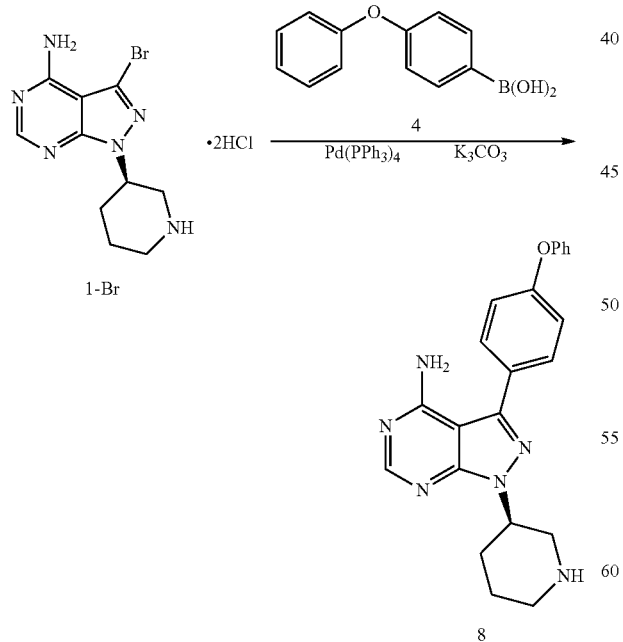

To a mixed solvent of 1,4-dioxane (200 mL) and water (80 mL) were added the dihydrochloride of the compound of Formula 1-Br (20 g, 0.054 mol), the compound of Formula 4 (17.35 g, 0.081 mol) and potassium carbonate (26.14 g, 0.19 mol). After bubbling with nitrogen gas for 20 min, Pd(PPh$_3$)$_4$ (0.62 g, 5.4×10$^{-4}$ mol) was added, and bubbling with nitrogen gas was continued for 5 min. The reaction solution was heated to reflux for 5 h under stirring, and then concentrated. Ethyl acetate (100 mL) and water (100 mL) were added to the residue. The resulting solution was layered after the pH was adjusted to 2 to 3 with hydrochloric acid, and then the aqueous phase was extracted once with ethyl acetate (100 mL). After liquid separation, dichloromethane (200 mL) was added to the aqueous phase, and the pH was adjusted to 9 to 10 with 6N sodium hydroxide solution. The resulting solution was stirred for liquid separation. The organic layer was dried over anhydrous sodium sulfate, and the solvent was evaporated to dryness to afford 16.8 g of an off-white solid in 80.4% yield.

Example 17

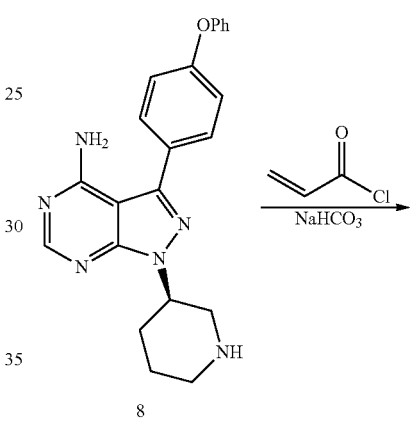

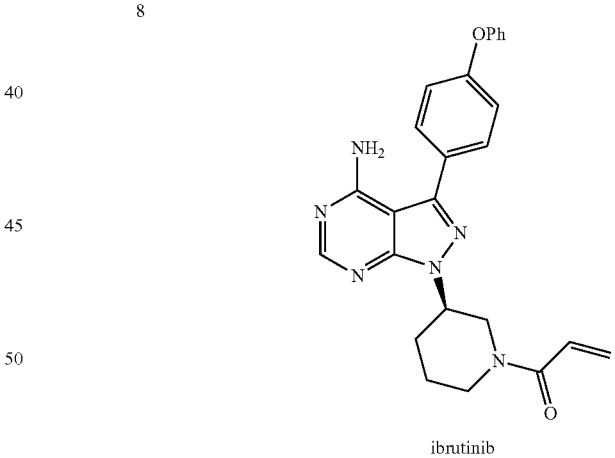

ibrutinib

The compound of Formula 8 (10 g, 0.026 mol) was dissolved in 2-methyltetrahydrofuran (100 mL), and a 7% aqueous solution (62 mL) of sodium bicarbonate (4.37 g, 0.052 mol) was added under the protection of nitrogen atmosphere. The reaction temperature was then reduced to −5° C., and a solution of acryloyl chloride (2.34 g, 0.026 mol) in 2-methyltetrahydrofuran (10 mL) was slowly added dropwise. After completing the addition, the reaction temperature was kept below 0° C., and meanwhile the reaction solution was stirred for 1 h, and then layered. After the aqueous phase was extracted with 2-methyltetrahydrofuran (100 mL), the organic phases were combined, washed sequentially with a 7% aqueous solution (50 mL) of sodium bicarbonate and water (50 mL), dried over anhydrous sodium sulfate, and then concentrated in vacuo to dryness to afford 10.5 g of a white foamy solid in 92.1% yield. The solid was recrystallized from ethyl acetate and n-heptane to afford 10.0 g of a white crystal in 95.0% yield, 99.6% chemical purity and 99.5% optical purity.

Example 18

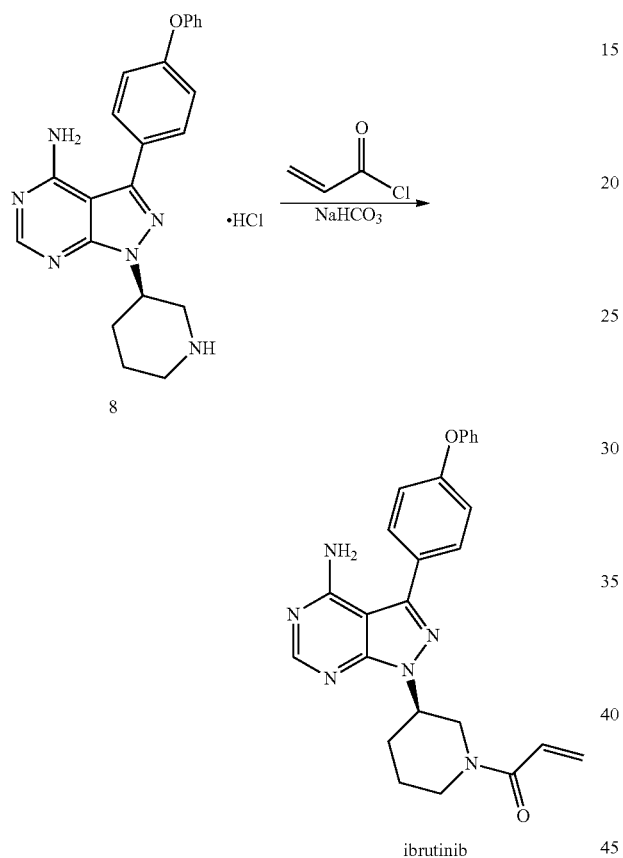

The hydrochloride of the compound of Formula 8 (11 g, 0.026 mol) was dissolved in 2-methyltetrahydrofuran (100 mL), and a 7% aqueous solution (72 mL) of sodium bicarbonate (5.04 g, 0.06 mol) was added under the protection of nitrogen atmosphere. The reaction temperature was then reduced to −5° C., and a solution of acryloyl chloride (2.34 g, 0.026 mol) in 2-methyltetrahydrofuran (10 mL) was slowly added dropwise. After completing the addition, the reaction temperature was kept below 0° C., and meanwhile the reaction solution was stirred for 1 h, and then layered. After the aqueous phase was extracted with 2-methyltetrahydrofuran (50 mL), the organic phases were combined, washed sequentially with a 7% aqueous solution (50 mL) of sodium bicarbonate and water (50 mL), dried over anhydrous sodium sulfate, and concentrated in vacuo to dryness to afford 10.2 g of a white foamy solid in 89.9% yield. The solid was recrystallized from ethyl acetate and n-heptane to afford 9.7 g of a white crystal in 95.0% yield, 99.7% chemical purity and 99.6% optical purity.

What is claimed is:

1. A process for preparing ibrutinib, comprising

Step 1: reacting a compound of Formula 1 with a compound of Formula 4 in the presence of a base and a catalyst to produce a compound of Formula 8,

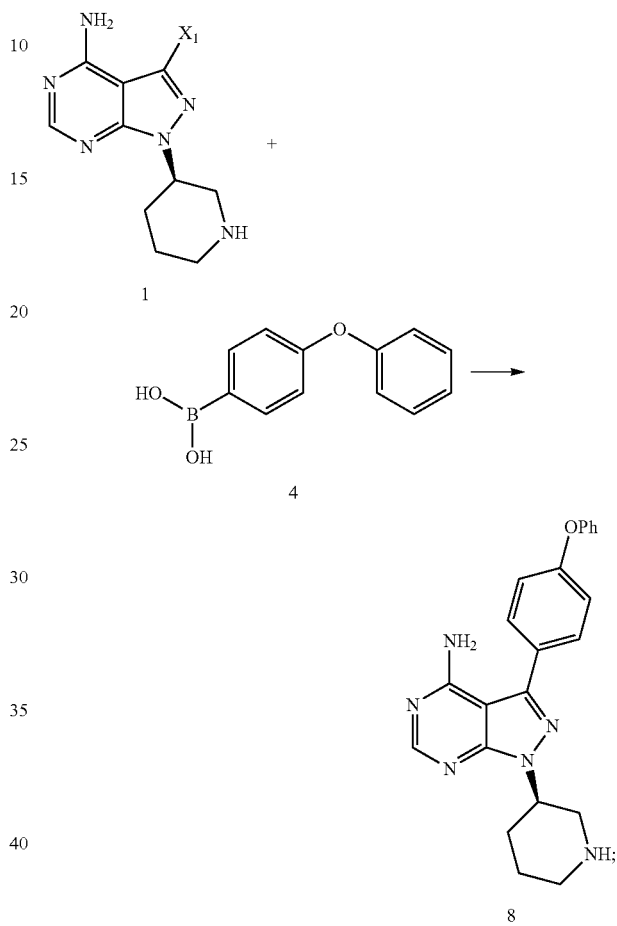

Step 2: reacting the compound of Formula 8 with a compound of Formula 2-1 in the presence of a base to produce ibrutinib,

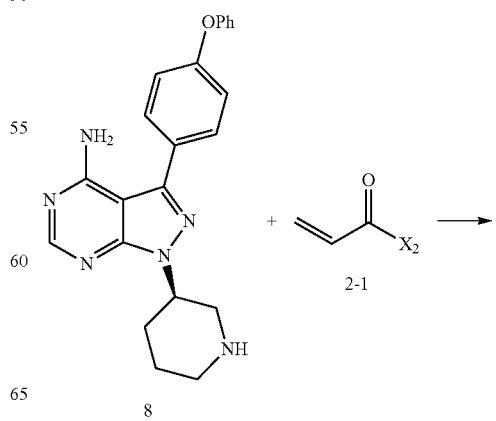

-continued

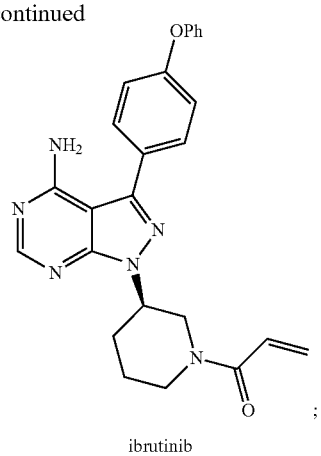

ibrutinib wherein $X_1$ is independently selected from the group consisting of Cl, Br and I; $X_2$ is independently selected from the group consisting of Cl and Br.

2. The process for preparing ibrutinib according to claim 1, wherein the catalyst in step 1 is selected from the group consisting of $Pd(PPh_3)_4$, $PdCl_2(PPh_3)_2$, $PdCl_2(PhCN)_2$, $Pd(OAc)_2$, Pd/C and $PdCl_2(dppf)_2$, preferably $Pd(PPh_3)_4$; and/or
wherein the base in step 1 is potassium carbonate, sodium carbonate, cesium carbonate, potassium acetate, sodium acetate, potassium phosphate, sodium phosphate, sodium bicarbonate, potassium bicarbonate, sodium hydroxide, potassium hydroxide, sodium hydride or potassium hydride; and/or
wherein a reaction solvent in step 1 is a mixed solvent of tetrahydrofuran, 1,4-dioxane, acetonitrile, acetone, N,N-dimethylformamide, dimethylsulfoxide, N-methylpyrrolidone or ethylene glycol dimethyl ether and water; and/or
wherein the base in step 2 is potassium carbonate, sodium carbonate, sodium bicarbonate, potassium bicarbonate, sodium hydroxide, potassium hydroxide, potassium hydride, sodium hydride, triethylamine, dimethylpyridine, diisopropylethylamine, or 1,8-diazabicyclo[5.4.0]undec-7-ene; and/or
wherein a reaction solvent in step 2 is tetrahydrofuran, 2-methyltetrahydrofuran, N,N-dimethylformamide, acetonitrile or acetone.

3. The process for preparing ibrutinib according to claim 1, further comprising
reacting a compound of Formula 5 with a compound of Formula 6 in the presence of a Mitsunobu reaction reagent to produce a compound of Formula 7, and deprotecting the compound of Formula 7 in the presence of an acid to produce the compound of Formula 1:

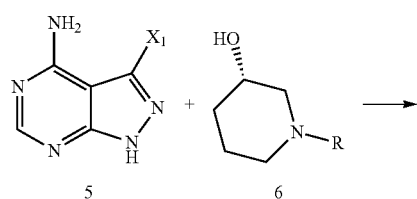

-continued

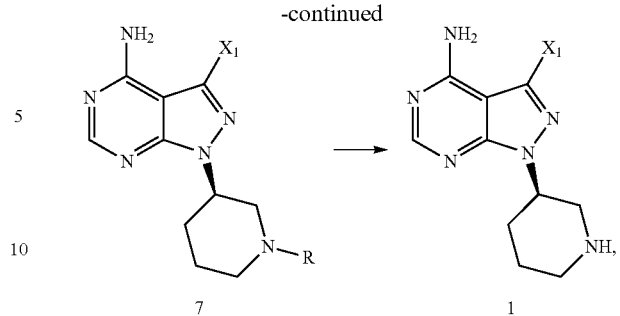

wherein R is an amino protecting group, preferably tert-butoxycarbonyl; and $X_1$ is independently selected from the group consisting of Cl, Br and I.

4. The process for preparing ibrutinib according to claim 3, wherein the Mitsunobu reaction reagent is composed of a first reagent selected from the group consisting of triphenylphosphine, tributylphosphine and trimethylphosphine, and a second reagent selected from the group consisting of diisopropyl azodicarboxylate, di-tert-butyl azodicarboxylate, diethyl azodicarboxylate, di-p-chlorobenzyl azodicarboxylate, 1,1'-(azodicarbonyl)dipiperidine, N,N,N',N'-tetraisopropylazodicarboxamide, N,N,N',N'-tetramethylazodicarboxamide and 4,7-dimethyl-3,4,5,6,7,8-hexahydro-1,2,4,7-tetrazocin-3,8-dione.

5. The process for preparing ibrutinib according to claim 3, wherein a solvent used for preparing the compound of Formula 7 is selected from the group consisting of tetrahydrofuran, N,N-dimethylformamide, dimethylsulfoxide, N-methylpyrrolidone, acetonitrile and 1,4-dioxane.

6. The process for preparing ibrutinib according to claim 3, wherein the acid used when deprotecting the compound of Formula 7 is selected from the group consisting of hydrochloric acid, hydrobromic acid, sulfuric acid, phosphoric acid, acetic acid, methanesulfonic acid and trifluoroacetic acid.

7. The process of claim 1, wherein $X_1$ is Cl or Br.

8. The process of claim 2, wherein the base in step 1 is potassium phosphate or potassium carbonate.

9. The process of claim 2, wherein the reaction solvent in step 1 is a mixed solvent of 1,4-dioxane and water or a mixed solvent of ethylene glycol dimethyl ether and water.

10. The process of claim 2, wherein the base in step 2 is sodium bicarbonate and potassium bicarbonate.

11. The process of claim 2, wherein the reaction solvent in step 2 is 2-methyltetrahydrofuran.

12. The process of claim 3, wherein $X_1$ is Cl and Br.

13. The process of claim 4, wherein the Mitsunobu reaction reagent is composed of triphenylphosphine and diisopropyl azodicarboxylate.

14. The process of claim 5, wherein the solvent used for preparing the compound of Formula 7 is tetrahydrofuran.

15. The process of claim 6, wherein the acid used when deprotecting the compound of Formula 7 is hydrochloric acid.

* * * * *